(12) United States Patent
Baker, Jr.

(10) Patent No.: US 8,109,882 B2
(45) Date of Patent: Feb. 7, 2012

(54) SYSTEM AND METHOD FOR VENOUS PULSATION DETECTION USING NEAR INFRARED WAVELENGTHS

(75) Inventor: Clark R. Baker, Jr., Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1339 days.

(21) Appl. No.: 11/716,132

(22) Filed: Mar. 9, 2007

(65) Prior Publication Data
US 2008/0221463 A1  Sep. 11, 2008

(51) Int. Cl.
*A61B 5/02* (2006.01)

(52) U.S. Cl. ........................ 600/500; 600/310

(58) Field of Classification Search .......... 600/500–502, 600/323, 507, 324–328
See application file for complete search history.

(56) References Cited

U.S. PATENT DOCUMENTS

| | | | |
|---|---|---|---|
| 3,998,550 A | 12/1976 | Konishi et al. |
| 4,066,068 A | 1/1978 | Nilsson et al. |
| 4,364,008 A | 12/1982 | Jacques |
| 4,380,439 A | 4/1983 | Kreitenberg |
| 4,711,244 A | 12/1987 | Kuzara |
| 4,723,554 A | 2/1988 | Oman et al. |
| 4,759,369 A | 7/1988 | Taylor |
| 4,805,623 A | 2/1989 | Jobsis |
| 4,824,242 A | 4/1989 | Frick et al. |
| 4,850,365 A | 7/1989 | Rosenthal |
| 4,859,057 A | 8/1989 | Taylor et al. |
| 4,860,753 A | 8/1989 | Amerena |
| 4,863,265 A | 9/1989 | Flower et al. |
| 4,867,557 A | 9/1989 | Takatani et al. |
| 4,883,055 A | 11/1989 | Merrick |
| 4,907,594 A | 3/1990 | Muz |
| 4,911,167 A | 3/1990 | Corenman et al. |
| 4,926,867 A | 5/1990 | Kanda et al. |
| 4,955,379 A | 9/1990 | Hall |
| 4,968,137 A | 11/1990 | Yount |
| 5,025,791 A | 6/1991 | Niwa |
| 5,057,695 A | 10/1991 | Hirao et al. |
| 5,086,781 A | 2/1992 | Bookspan |
| 5,111,817 A | 5/1992 | Clark et al. |
| 5,146,091 A | 9/1992 | Knudson |
| 5,224,478 A | 7/1993 | Sakai et al. |

(Continued)

FOREIGN PATENT DOCUMENTS

CA  2353007 A1  6/2000

(Continued)

OTHER PUBLICATIONS

Aoyagi, Takuro, Pulse oximetry: its invention, theory, and future, 2003, Journal of Anesthesia, 17:259-266.*

(Continued)

*Primary Examiner* — Miranda Le
*Assistant Examiner* — Michael R Bloch (57) ABSTRACT

Methods and systems for detecting venous pulsation are provided. In accordance with an exemplary embodiment of the present technique, there is provided a method for detecting venous pulsation, including acquiring a first signal corresponding to absorption at a first near-infrared wavelength, acquiring a second signal corresponding to absorption at a second near-infrared wavelength, deriving an offset metric from the first and second signals, and detecting the presence of venous pulsation based on the offset metric. The method further includes correcting calculations of physiological parameters such as, for example, blood oxygen saturation, when venous pulsation is detected.

21 Claims, 4 Drawing Sheets

U.S. PATENT DOCUMENTS

| | | | |
|---|---|---|---|
| 5,251,632 A | 10/1993 | Delpy |
| 5,263,244 A | 11/1993 | Centa et al. |
| 5,267,562 A | 12/1993 | Ukawa et al. |
| 5,267,563 A | 12/1993 | Swedlow et al. |
| 5,277,181 A | 1/1994 | Mendelson et al. |
| 5,278,627 A | 1/1994 | Aoyagi et al. |
| 5,279,295 A | 1/1994 | Martens et al. |
| 5,282,467 A | 2/1994 | Piantadosi et al. |
| 5,297,548 A | 3/1994 | Pologe |
| 5,299,120 A | 3/1994 | Kaestle |
| 5,329,922 A | 7/1994 | Atlee, III |
| 5,337,745 A | 8/1994 | Benaron |
| 5,337,937 A | 8/1994 | Blank et al. |
| 5,348,004 A | 9/1994 | Hollub |
| 5,348,005 A | 9/1994 | Merrick et al. |
| 5,349,519 A | 9/1994 | Kaestle |
| 5,355,880 A | 10/1994 | Thomas et al. |
| 5,355,882 A | 10/1994 | Ukawa et al. |
| 5,377,674 A | 1/1995 | Kuestner |
| 5,390,670 A | 2/1995 | Centa et al. |
| 5,392,777 A | 2/1995 | Swedlow et al. |
| 5,396,893 A | 3/1995 | Oberg et al. |
| 5,402,777 A | 4/1995 | Warring et al. |
| 5,402,778 A | 4/1995 | Chance |
| 5,408,998 A | 4/1995 | Mersch |
| 5,417,207 A | 5/1995 | Young et al. |
| 5,458,562 A | 10/1995 | Cooper |
| 5,485,847 A | 1/1996 | Baker, Jr. |
| 5,490,505 A | 2/1996 | Diab et al. |
| 5,499,627 A | 3/1996 | Steuer et al. |
| 5,503,148 A | 4/1996 | Pologe et al. |
| 5,517,988 A | 5/1996 | Gerhard |
| 5,522,388 A | 6/1996 | Ishikawa et al. |
| 5,524,617 A | 6/1996 | Mannheimer |
| 5,575,285 A | 11/1996 | Takanashi et al. |
| 5,584,299 A | 12/1996 | Sakai et al. |
| 5,595,176 A | 1/1997 | Yamaura |
| 5,615,689 A | 4/1997 | Kotler |
| 5,645,059 A | 7/1997 | Fein et al. |
| 5,662,106 A | 9/1997 | Swedlow et al. |
| 5,685,299 A | 11/1997 | Diab et al. |
| 5,687,721 A | 11/1997 | Kuhls |
| 5,690,104 A | 11/1997 | Kanemoto et al. |
| 5,701,902 A | 12/1997 | Vari et al. |
| 5,715,816 A | 2/1998 | Mainiero et al. |
| 5,720,284 A | 2/1998 | Aoyagi et al. |
| 5,735,284 A | 4/1998 | Tsoglin et al. |
| 5,743,261 A | 4/1998 | Mainiero et al. |
| 5,743,263 A | 4/1998 | Baker, Jr. |
| 5,743,349 A | 4/1998 | Steinberg |
| 5,746,206 A | 5/1998 | Mannheimer |
| 5,747,789 A | 5/1998 | Godik |
| 5,755,672 A | 5/1998 | Arai et al. |
| 5,766,127 A | 6/1998 | Pologe et al. |
| 5,788,643 A | 8/1998 | Feldman |
| 5,803,908 A | 9/1998 | Steuer et al. |
| 5,810,723 A | 9/1998 | Aldrich |
| 5,817,008 A | 10/1998 | Rafert et al. |
| 5,827,181 A | 10/1998 | Dias et al. |
| 5,830,137 A | 11/1998 | Scharf |
| 5,833,602 A | 11/1998 | Osemwota |
| 5,853,364 A | 12/1998 | Baker, Jr. et al. |
| 5,860,919 A | 1/1999 | Kiani-Azarbayjany et al. |
| 5,871,694 A | 2/1999 | Beden et al. |
| 5,891,025 A | 4/1999 | Buschmann et al. |
| 5,902,235 A | 5/1999 | Lewis et al. |
| 5,906,582 A | 5/1999 | Kondo et al. |
| 5,934,277 A | 8/1999 | Mortz |
| 6,018,673 A | 1/2000 | Chin et al. |
| 6,064,898 A | 5/2000 | Aldrich |
| 6,073,041 A | 6/2000 | Hu et al. |
| 6,125,297 A | 9/2000 | Siconolfi |
| 6,149,591 A | 11/2000 | Henderson et al. |
| 6,149,597 A | 11/2000 | Kamiyama |
| 6,151,107 A | 11/2000 | Schollermann et al. |
| 6,151,518 A | 11/2000 | Hayashi |
| 6,178,342 B1 | 1/2001 | Thompson et al. |
| 6,178,343 B1 | 1/2001 | Bindszus et al. |
| 6,216,021 B1 | 4/2001 | Franceschini et al. |
| 6,222,189 B1 | 4/2001 | Misner et al. |
| 6,230,035 B1 | 5/2001 | Aoyagi et al. |
| 6,246,894 B1 | 6/2001 | Steuer et al. |
| 6,258,038 B1 | 7/2001 | Haryadi et al. |
| 6,263,222 B1 | 7/2001 | Diab et al. |
| 6,272,363 B1 | 8/2001 | Casciani et al. |
| 6,278,889 B1 | 8/2001 | Robinson |
| 6,280,396 B1 | 8/2001 | Clark et al. |
| 6,285,896 B1 | 9/2001 | Tobler et al. |
| 6,299,583 B1 | 10/2001 | Eggers et al. |
| 6,330,468 B1 | 12/2001 | Scharf |
| 6,334,065 B1 | 12/2001 | Al-Ali et al. |
| 6,336,044 B1 | 1/2002 | Ghiassi et al. |
| 6,339,715 B1 | 1/2002 | Bahr et al. |
| 6,370,426 B1 | 4/2002 | Campbell et al. |
| 6,374,129 B1 | 4/2002 | Chin et al. |
| 6,381,480 B1 | 4/2002 | Stoddart et al. |
| 6,385,471 B1 | 5/2002 | Mortz |
| 6,393,310 B1 | 5/2002 | Kuenstner |
| 6,393,311 B1 | 5/2002 | Edgar, Jr. et al. |
| 6,397,093 B1 | 5/2002 | Aldrich |
| 6,400,971 B1 | 6/2002 | Finarov et al. |
| 6,402,690 B1 | 6/2002 | Rhee et al. |
| 6,406,267 B1 | 6/2002 | Mondiere |
| 6,411,832 B1 | 6/2002 | Guthermann |
| 6,415,236 B2 | 7/2002 | Kobayashi et al. |
| 6,438,399 B1 * | 8/2002 | Kurth ........................... 600/323 |
| 6,442,408 B1 | 8/2002 | Wenzel et al. |
| 6,449,501 B1 | 9/2002 | Reuss |
| 6,461,165 B1 | 10/2002 | Takanashi et al. |
| 6,466,807 B1 | 10/2002 | Dobson et al. |
| 6,480,729 B2 | 11/2002 | Stone |
| 6,488,677 B1 | 12/2002 | Bowman et al. |
| 6,494,576 B1 | 12/2002 | L'Esperance |
| 6,501,974 B2 | 12/2002 | Huiku |
| 6,512,936 B1 | 1/2003 | Monfre et al. |
| 6,519,486 B1 | 2/2003 | Edgar, Jr. et al. |
| 6,526,297 B1 | 2/2003 | Merilainen |
| 6,584,336 B1 | 6/2003 | Ali et al. |
| 6,587,704 B1 | 7/2003 | Fine et al. |
| 6,591,122 B2 | 7/2003 | Schmitt |
| 6,592,574 B1 | 7/2003 | Shimmick et al. |
| 6,600,946 B1 | 7/2003 | Rice |
| 6,606,509 B2 | 8/2003 | Schmitt |
| 6,615,064 B1 | 9/2003 | Aldrich |
| 6,615,065 B1 | 9/2003 | Barrett et al. |
| 6,622,095 B2 | 9/2003 | Kobayashi et al. |
| 6,635,491 B1 | 10/2003 | Khalil et al. |
| 6,636,759 B2 | 10/2003 | Robinson |
| 6,643,543 B2 | 11/2003 | Takehara et al. |
| 6,647,280 B2 | 11/2003 | Bahr et al. |
| 6,650,917 B2 | 11/2003 | Diab et al. |
| 6,654,620 B2 | 11/2003 | Wu et al. |
| 6,668,181 B2 | 12/2003 | Wenzel et al. |
| 6,671,526 B1 | 12/2003 | Aoyagi et al. |
| 6,675,029 B2 | 1/2004 | Monfre et al. |
| 6,687,519 B2 | 2/2004 | Steuer et al. |
| 6,702,752 B2 | 3/2004 | Dekker |
| 6,714,803 B1 | 3/2004 | Mortz |
| 6,714,804 B2 | 3/2004 | Al-Ali et al. |
| 6,754,515 B1 | 6/2004 | Pologe |
| 6,770,028 B1 | 8/2004 | Ali et al. |
| 6,777,240 B2 | 8/2004 | Hazen et al. |
| 6,780,158 B2 | 8/2004 | Yarita |
| 6,801,799 B2 | 10/2004 | Mendelson |
| 6,810,277 B2 | 10/2004 | Edgar, Jr. et al. |
| 6,839,585 B2 | 1/2005 | Lowery et al. |
| 6,842,635 B1 | 1/2005 | Parker |
| 6,845,256 B2 | 1/2005 | Chin et al. |
| 6,849,046 B1 | 2/2005 | Eyal-Bickels |
| 6,859,658 B1 | 2/2005 | Krug |
| 6,879,850 B2 | 4/2005 | Kimball |
| 6,898,452 B2 | 5/2005 | Al-Ali et al. |
| 6,947,780 B2 | 9/2005 | Scharf |
| 6,947,781 B2 | 9/2005 | Asada |
| 6,950,699 B2 | 9/2005 | Manwaring et al. |
| 6,970,792 B1 * | 11/2005 | Diab ........................... 702/32 |
| 6,987,994 B1 | 1/2006 | Mort |

| | | |
|---|---|---|
| 7,039,538 B2 | 5/2006 | Baker, Jr. |
| 7,194,293 B2 | 3/2007 | Baker, Jr. |
| 7,209,774 B2 | 4/2007 | Baker, Jr. |
| 7,236,811 B2 | 6/2007 | Schmitt |
| 7,239,902 B2 | 7/2007 | Schmitt et al. |
| 7,263,395 B2 | 8/2007 | Chan et al. |
| 7,277,741 B2 | 10/2007 | Debreczeny et al. |
| 2001/0020122 A1 | 9/2001 | Steuer et al. |
| 2003/0060693 A1 | 3/2003 | Monfre et al. |
| 2004/0127777 A1 | 7/2004 | Ruchti et al. |
| 2004/0147034 A1 | 7/2004 | Gore et al. |
| 2004/0230106 A1 | 11/2004 | Schmitt et al. |
| 2004/0249252 A1 | 12/2004 | Fine et al. |
| 2005/0197552 A1 | 9/2005 | Baker, Jr. |
| 2005/0197579 A1* | 9/2005 | Baker, Jr. .................. 600/473 |
| 2005/0256386 A1 | 11/2005 | Chan et al. |
| 2006/0020181 A1 | 1/2006 | Schmitt |
| 2006/0084864 A1 | 4/2006 | Schmitt et al. |
| 2006/0167350 A1 | 7/2006 | Monfre et al. |
| 2006/0200015 A1 | 9/2006 | Baker, Jr. |
| 2006/0224053 A1 | 10/2006 | Black et al. |
| 2006/0253007 A1 | 11/2006 | Cheng et al. |
| 2006/0253016 A1 | 11/2006 | Baker, Jr. et al. |
| 2006/0276696 A1 | 12/2006 | Schurman |
| 2007/0032714 A1* | 2/2007 | Mannheimer ............. 600/323 |
| 2007/0077200 A1 | 4/2007 | Baker, Jr. |
| 2007/0100220 A1 | 5/2007 | Baker, Jr. |
| 2007/0106137 A1* | 5/2007 | Baker et al. ................ 600/336 |
| 2007/0118027 A1 | 5/2007 | Baker, Jr. et al. |
| 2007/0129614 A1 | 6/2007 | Schmitt et al. |
| 2007/0208242 A1 | 9/2007 | Baker, Jr. |
| 2008/0077022 A1 | 3/2008 | Baker |
| 2008/0221417 A1 | 9/2008 | Baker et al. |
| 2008/0221462 A1 | 9/2008 | Baker |

FOREIGN PATENT DOCUMENTS

| | | |
|---|---|---|
| DE | 19855521 A1 | 6/2000 |
| EP | 1135184 A1 | 6/2000 |
| EP | 1184663 A2 | 3/2002 |
| FR | 2710517 | 4/1995 |
| JP | 4-40940 | 2/1992 |
| JP | 5-329163 | 12/1993 |
| JP | 11-244266 | 9/1999 |
| JP | 2004 081427 A | 3/2004 |
| WO | WO 93/13706 A2 | 7/1993 |
| WO | WO 95/19562 A | 7/1995 |
| WO | WO 98/34097 | 8/1998 |
| WO | WO 00/32262 A1 | 6/2000 |
| WO | WO 00/71025 A1 | 11/2000 |
| WO | WO 01/16577 A1 | 3/2001 |
| WO | WO 03/010510 A | 2/2003 |
| WO | WO 2005/041765 A | 5/2005 |

OTHER PUBLICATIONS

Burmeister, Jason and Mark Arnold, Spectroscopic Considerations for Noninvasive Blood Glucose Measurements with Near Infrared Spectroscopy, Mar. 17, 2005, Infrared Spectroscopy, p. 1.*
Schmitt, Joeseph, Zhou Guarn-Xiong and Justin Miller, Measurement of blood hematocrit by dual-wavelength near-IR photoplethysmography, The International Society for Optical Engineering, 1992, 1641:150-161.*
U.S. Appl. No. 11/528,154, filed Sep. 27, 2006, Debreczeny et al.
U.S. Appl. No. 11/528,218, filed Sep. 27, 2006, Campbell, et al.
U.S. Appl. No. 11/529,024, filed Sep. 28, 2006, Agashe, et al.
U.S. Appl. No. 11/541,010, filed Sep. 29, 2006, Baker, Jr., et al.
Wheeler, Owen H., "Near Infrared Spectra of Organic Compounds," Department of Chemistry, College of Agriculture and Mechanic Arts, University of Puerto Rico (Mar. 1929).
Pace, Nello, et al., "Studies on Body Composition: III. The body water and chemically combined nitrogen content in relation to fat content," Naval Medical Research Institute, Bethesda, Maryland (Jan. 11, 1945).
Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).
Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).
Forbes, R.M., et al., "The Composition of the Adult Human Body as Determined by Chemical Analysis," Division of Animal Nutrition, and the Department of Anatomy, University of Illinois, Jan. 19, 1953.
Buijs, K., et al., "Near-Infrared Studies of the Structure of Water. I. Pure Water," *The Journal of Chemical Physics*, vol. 39, No. 8, pp. 2035-2041 (Oct. 15, 1963).
Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).
Goldstein, R., et al., "The Near-Infrared Absorption of Liquid Water at Temperatures Between 27 and 209°C," *J. Quant. Spectrosc. Radiat. Transfer.*, vol. 4, pp. 441-451 (1964).
Ben-Gera, I., et al., "Influence of Fat Concentration on the Absorption Spectrum of Milk in the Near-Infrared Region," *Israel J. Agric. Res.*, Vo. 18, No. 3, pp. 117-124 (Jul. 1968).
Houseman, R.A., et al., "The measurement of total body water in living pigs by deuterium oxide dilution and its relation to body composition," *Br. J. Nutr.*, vol. 30, pp. 149-156 (1973).
Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).
Lesser, G.T., et al., "Body water compartments with human aging using fat-free mass as the reference standard," *Am J. Physiol Regul Integr Comp Physiol.*, vol. 236, pp. 215-220 (1979).
Sheng, Hwai-Ping, et al., "A review of body composition studies with emphasis on total body water and fat," *The American Journal of Clinical Nutrition*, vol. 32., pp. 630-647 (Mar. 1979).
Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-159 (1980).
Fomon, Samuel J., et al., "Body composition of reference children from birth to age 10 years," The American Journal of clinical Nutrition, vol. 35, pp. 1169-1175, (May 1982).
Lanza, Elaine, "Determination of Moisture, Protein, Fat, and Calories in Raw Pork and Beef by near Infrared Spectroscopy," *Journal of Food Science*, vol. 48, pp. 471-474 (1983).
Shields, R. G., Jr., et al., "Efficacy of Deuterium Oxide to Estimate Body Composition of Growing Swine"; *Journal of Animal Science*, vol. 57, No. 1, pp. 66-73, (1983).
Wolfgang, Arneth, "Multivariate Infrared and near-infrared Spectroscopy: rapid analysis of protein, fat and water in meat," *Food Res and Data Analysis, Proc from IUoST Symp, Oslo, Norway*, pp. 239-251 (1983).
Cohn, S.H., et al., "Assessment of cellular mass and lean body mass by noninvasive nuclear techniques," *J. Lab Clin Med.*, vol. 105, pp. 305-311 (1985).
Hannon, John P., et al., "Splenic red cell sequestration and blood volume measurements in conscious pigs," *Am J. Physiol.*, vol. 248, pp. R293-R301 (1985).
Potts, R.O., et al., "A Noninvasive, In Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).
Cox, Patrick, et al., "Variations in Lipids in Different Layers of Porcine Epidermis," *J. Invest Dermatol.*, vol. 87, pp. 741-744 (1986).
Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).
Hedberg, Chrisopher L., et al., "The Time Course of Lipid Biosynthesis in Pig Epidermis," *J. Invest Dermatol.*, vol. 91, pp. 169-174 (1988).
Hedberg, Christopher L., et al., "The nonpolar Lipids of Pig Epidermis," *J. Invest Dermatol.*, vol. 90, pp. 225-229 (1988).

Trapp, Scott A., et al., "An improved spectrophotometric bromide assay for the estimation of extracellular water volume," *Clinica Chimica Acta.*, vol. 181, pp. 207-212, (1989).

Bommannan, D., et al., "Examination of Stratum Corneum Barrier Function In Vivo by Infrared Spectroscopy," *J. Invest Dermatol*, vol. 95, pp. 403-408 (1990).

Hannon, John P., et al., "Normal pHysiological Values for Conscious Pigs Used in Biomedical Research," *Laboratory Animal Science*, vol. 40, No. 3, May 1990.

Mak, Vivien H.W., et al., "Oleic Acid Concentration and Effect in Human Stratum Corneum: Non-Invasive determination by Attenuated Total Reflectance Infrared Spectroscopy In Vivo," *Journal of Controlled Release*, vol. 12, pp. 67-75 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-1094, 1991.

Drummer, C., et al., "Effects of an acute saline infusion on fluid and electrolyte metabolism in humans," *Am J. Physiol.*, vol. 262, pp. F744-F754 (1992).

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Diaz-Carrillo, E., et al., "Near infrared calibrations for goat's milk components; protein, total casein, $\alpha_s$-, $\beta$- and $\kappa$-caseins, fat and lactose," *J. near Infrared Spectrosc.*, vol. 1, pp. 141-146 (1993).

Martin, K., "Direct Measurement of Moisture in Skin by NIR spectroscopy," *J. Soc. Cosmet. Chem.*, 44:249-261 (1993).

Richard, Stéphanie, et al., "Characterization of the Skin In Vivo by High Resolution Magnetic Resonance Imaging: Water Behavior and Age-Related Effects," *The Journal of Investigative Dermatology*, vol. 100, No. 5, pp. 705-709 (May 1993).

Thompson et al., "Can bioelectrical impedance be used to measure total body water in dialysis patients?", *Physiol. Meas.*, 14:455-461 (1993).

Bewig, Karen M., et al., "Discriminant Analysis of Vegetable Oils by Near-Infrared Reflectance Spectroscopy," *JAOCS*, vol. 71, No. 2, pp. 195-200 (Feb. 1994).

Kamishikiryo-Yamashita, Hiromi, et al, "Protein Content in Milk by Near-Infrared Spectroscopy," *Journal of Food Science*, vol. 59, No. 2, pp. 313-315 (1994).

Matcher, S. J., et al., "Absolute quantification of deoxyhaemoglobin concentration in tissue near infrared spectroscopy," *Phys. Med. Biol.*, vol. 39, pp. 1295-1312 (1994).

Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C., et al., "Protein composition of cornified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-72.

Warren, Joan L., et al., "The burden and Outcomes Associates with Dehydration among US Elderly, 1991," *American Journal of Public Health*, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," *Anesth Analg.*, vol. 80, pp. 135-142, (1995).

Kisch, Hille, et al., "Accuracy and reproducibility of the measurement of actively circulating blood vol. with an integrated fiberoptic monitoring system," *Critical Care Medicine*, vol. 23, No. 5, pp. 885-893 (1995).

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Quiniou, N., et al., "Prediction of Tissular Body Composition from Protein and Lipid Deposition in Growing Pigs," *J. Anim. Sci.*, vol. 73, pp. 1567-1575, (1995).

Avis, N.J., et al.; "In vitro multifrequency electrical impedance measurements and modeling of the cervix in late pregnancy", *Physiological Measurement*, vol. 17, pp. A97-A103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet,vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr.* 64(suppl):489S-97S (1996).

Kumar, Gitesh, et al., "Non-Invasive Optical Assessment of Tissue Hydration," *International conference on Biomedical Engineering*, Jun. 3-5, 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).
Thomas, B. J., et al., "Bioimpedance Spectrometry in the Determination of Body Water Compartments: Accuracy and Clinical Significance," *Appl. Radial. Isot.*, vol. 49, No. 5/6, pp. 447-455, (1998).
Wilhelm, K.P., "Possible Pitfalls in Hydration Measurements," *Skin Bioengineering Techniques and Applications in Dermatology and Cosmetology*, vol. 26, pp. 223-234 (1998).
Vrhovski, Bernadette, et al., "Biochemistry of tropoelastin," *Eur. J. Biochem.*, vol. 258, pp. 1-18 (1998).
Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).
Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).
Fornetti, Willa C., et al., "Reliability and validity of body composition measures in female athletes," Journal of Applied Physiology, vol. 87, pp. 1114-1122, (1999).
Fusch, Christoph, et al., "Neonatal Body COmponsition: Dual-Energy X-Ray Absorptiometry, Magnetic Resonance Imaging, and Three-Dimensional Chemical Shift Imaging versus Chemical Analysis in Piglets," *Pediatric Research*, vol. 46, No. 4, pp. 465-473 (1999).
Gudivaka, R., et al., "Single- and multifrequency models for bioelectrical impedance analysis of body water compartments," *J. Appl. Physiol.*, vol. 87, No. 3, pp. 1087-1096 (1999).
Jennings, Graham, et al., "The Use of infrared Spectrophotometry for Measuring Body Water Spaces," vol. 45, No. 7, pp. 1077-1081 (1999).
Kalantar-Zadeh, Kamyar, et al., "Near infra-red interactance for nutritional assessment of dialysis patients," *Nephroi Dial Transplant*, vol. 14, pp. 169-175 (1999).
Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).
Lange, Neale R., et al., "The measurement of lung water, " *Critical Care*, vol. 3, pp. R19-R24 (1999).
Marken Lichtenbelt, Wouter D. Van, et al., "Increased extracellular water compartment, relative to intracellular water compartment, after weight reduction," *Journal of Applied Physiology*, vol. 87, pp. 294-298 (1999).
Rennie, Michael J., "Perspectives—Teasing out the truth about collagen," *Journal of Physiology*, vol. 521, p. 1 (1999).
Sowa et al., "New-infrared spectroscopic assessment of tissue hydration following surgery", *Journal of Surgical Research*, 86:62-69 (1999).
Wagner, J.R., et al., "Analysis of Body Composition Changes of Swine During Growth and Development," *J. Anim. Sci.*, vol. 77, pp. 1442-1466 (1999).
Wang, Zimian, et al., "Hydration of fat-free body mass: new physiological modeling approach," *Am. J. Physiol.*, vol. 276, pp. E995-E1003 (1999).
Wang, Zimian, et al., "Hydration of fat-free body mass: review and critique of a classic body-composition constant," *Am J. Clin. Nutr.*, vol. 69, pp. 833-841 (1999).
Ward, L., et al., "Multiple frequency bioelectrical impedance analysis: a cross-validation study of the inductor circuit and Cole models," *Physiol. Meas.*, vol. 20, pp. 333-347 (1999).
Well, Jonathan CK, et al., "Four-component model of body composition in children: density and hydration of fat-free mass and comparison with simpler models," *Am J. Clin. Nutr.*, vol. 69, pp. 904-912 (1999).
Butte, Nancy F., et al., "Body Composition during the First 2 Years of Life; An Updated Reference," *Pediatric Research*, vol. 47, No. 5, pp. 578-585 (2000).
Feigenbaum, Matthew S., et al., "Contracted Plasma and Blood Volume in Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).
Lucassen, G., et al., "Water Content and Water Profiles in Skin Measured by FTIR and Raman Spectroscopy," *Proc. SPIE*, vol. 4162, pp. 39-45 (2000).
Plank, L. D., et al., "Similarity of Changes in Body Composition in Intensive Care Patients following Severe Sepsis or Major Blunt Injury," *Annals New York Academy of Sciences*, pp. 592-602 (2000).
Ritz, P., et al., "Body Water Spaces and Cellular Hydration during Healthy Aging," *Annals New York Academy of Sciences*, pp. 474-483 (2000).
Schoeller, Dale, "Bioelectrical Impedance Analysis—What does it measure?" *Annals New York Academy of Sciences*, pp. 159-162 (2000).
Starcher, Barry C., "Lung Elastin and Matrix," *Chest*, vol. 117, No. 5, pp. 229S-234S, May 2000 Supplement.
Zembrzuski, Cora, "Nutrition and Hydration," Best Practices in Nursing Care to Older Adults, The Hartford Institute for Geriatric Nursing, vol. 2, No. 2, Sep. 2000, 2 pages.
Attas, Michael, et al., "Visualization of cutaneous hemoglobin oxygenation and skin hydration using near-infrared spectroscopic imaging," *Skin Research and Technology*, vol. 7, pp. 238-245, (2001).
Bray, George A., et al., "Evaluation of body fat in fatter and leaner 10-y-old African American and white children: the Baton Rouge Children's Study," *Am J. Clin Nutr*, vol. 73, pp. 687-702 (2001).
Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M-380 (2001).
Divert, Victor E., "Body Thermal State Influence on Local Skin Thermosensitivity," *International Journal of Circumpolar Health*, vol. 60, pp. 305-311 (2001).
Du, Y., et al., "Optical properties of porcine skin dermis between 900 nm and 1500 nm," *Phys. Med. Biol.*, vol. 46, pp. 167-181 (2001).
Endo, Yutaka, et al., "Water drinking causes a biphasic change in blood composition in humans," *Pflügers Arch—Eur J. Physiol*, vol. 442, pp. 362-368 (2001).
Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).
Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).
Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).
Kamba, Masayuki, et al., "Proton magnetic resonance spectroscopy for assessment of human body composition," *Am J. Clin. Nutr.*, vol. 73, pp. 172-176 (2001).
Lever, M., et al., "Some ways of looking at compensatory kosmotropes and different water environments," *Comparative Biochemistry and Physiolog.*, vol. 130, Part A, pp. 471-486, (2001).
Mingrone, G., et al., "Unreliable use of standard muscle hydration value in obesity," *Am J. Physiol Endocrinal Metab.*, vol. 280, pp. E365-E371, (2001).
Ritz, Patrick, "Chronic Cellular Dehydration in the Aged Patient," *Journal of Gerontology*, vol. 56A, No. 6, pp. M349-M352 (2001).
Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).
Schnickel, A.P., et al., "Evaluation of alternative measures of pork carcass composition," *J. Anim. Sci.*, vol. 79, pp. 1093-1119, (2001).
Sowa et al., "Near infrared spectroscopic assessment of hemodynamic changes in the early post-burn period," *Burns*, 27(3):241-9 (2001).
Troy, Tamara L., et al., "Optical properties of human skin in the near infrared wavelength range of 1000 to 2200nm," *Journal of Biomedical Optics*, vol. 6, No. 2, pp. 167-176 (Apr. 2001).

Tsukahara, K., et al., "Dermal fluid translocation is an important determinant of the diurnal variation in human skin thickness," *British Journal of Dermatology*, vol. 145, pp. 590-596 (2001).

Vescovi, Jason D., et al., "Evaluation of the BOD POD for estimating percentage body fat in a heterogeneous group of adult humans," *Eur J. Appl. Physiol.*, vol. 85, pp. 326-332 (2001).

Wang, Zimian, et al., "Magnitude and variation of ratio of total body potassium to fat-free mass: a cellular level modeling study," *Am J. Physiol. Endocrinal. Metab*, vol. 281, pp. E1-E7, (2001).

Watson, Walter, "Hydration of fat-free body mass: new physiological modeling approach," *Am J. Physiol. Endocrinol. Metab.*, Letters to the Editor, vol. 278, pp. E752-E753 (2001).

Attas, E. Michael, et al., "Near-IR Spectroscopic Imaging for Skin Hydration: The Long and the Short of It," *Biopolymers*, vol. 67, No. 2, pp. 96-106 (2002).

Attas, M. et al., "Long-Wavelength Near-Infrared Spectroscopic Imaging for In-Vivo Skin Hydration Measurements," *Vibrational spectroscopy* (28 Feb. 2002), vol. 28, No. 1, p. 37-43.

Blank, T.B., et al., "Clinical Results from a Non-Invasive Blood Glucose Monitor," *Photonics West 2002 Meeting*, San Jose, California, Jan. 19-25, 2002 (25 pages).

Chamney, Paul W., et al., "A new technique for establishing dry weight in hemodialysis patients via whole body bioimpedance," *Kidney International*, vol. 61, pp. 2250-2258 (2002).

Drobin, Dan, et al., "Kinetics of Isotonic and Hypertonic Plasma vol. Expanders," *Anesthesiology*, vol. 96, No. 6, pp. 1371-1380 (Jun. 2002).

Endo, Yutaka, et al., "Changes in Blood Pressure and Muscle Sympathetic Nerve Activity during Water Drinking in Humans," *Japanese Journal of Physiology*, vol. 52, pp. 421-427 (2002).

Haga, Henning A., et al., "Motor responses to stimulation during isoflurane anaesthesia in pigs," *Veterinary Anaesthesia and Analgesia*, vol. 29, pp. 69-75 (2002).

Klaus, Stephan, et al., "Assessment of fluid balance by measurement of skin tissue thickness during clinical anaesthesia," *Clin. Physiol. & Func. Im.*, vol. 22, pp. 197-201 (2002).

Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).

Perez-de-Sá, Valéria, et al., "Mild Hypothermia Has Minimal Effects on the Tolerance to Severe Progressive Normovolemic Anemia in Swine," *Anesthesiology*, Vo. 97, pp. 1189-1197 (2002).

Ponec, Maria, et al., "Charactrization of Reconstructed Skin Models," *Skin Pharmacol Appl Skin Physiol.*, vol. 15, Supplement 1, pp. 4-17, (2002).

Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).

Van Bommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).

Wong, William W., et al., "Evaluating body fat in girls and female adolescents: advantages and disadvantages of dual-energy X-ray absorptiometry," *Am J. Clin Nutr.*, vol. 76, pp. 384-389 (2002).

Baković, Darija, et al., "Spleen volume and blood flow response to repeated breath-hold apneas," *J. Appl. Physiol.*, vol. 95, pp. 1460-1466 (2003).

Bartok, Cynthia, et al., "Measurement of nutritional statusin simulated microgravity by bioelectrical impedance spectroscopy," *J. Appl. Physiol.*, vol. 95, pp. 225-232 (2003).

Bouwstra, Joke A., et al., "Water Distribution and Related Morphology in Human Stratum Corneum at Different Hydration Levels," *J. Invest Dermatol*, vol. 150, pp. 750-758 (2003).

Butte, Nancy F., et al., "Composition of gestational weight gain impacts maternal fat retention and infant birth weight," *Am J. Obstet Gynecol*, vol. 189, pp. 1423-1432 (2003).

Cloonan, Clifford C., "Don't Just Do Something, Stand There!: To Teach of not to Teach, That is the Question—Intravenous Fluid Resuscitation Training for Combat Lifesavers," *The Journal of TRAUMA, Injury, Infection, and Critical Care*, vol. 54, No. 5, pp. S20-S25 (May Supplement 2003).

Cook, Lynda S., "IV Vluid Resuscitation," *Journal of Infusion Nursing*, vol. 26, No. 5, pp. 296-303 (Sep./Oct. 2003).

Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).

Farstad, M., et al., "Fluid extravasation during cardiopulmonary bypass in piglets—effects of hypothermia and different cooling protocols," *Acta Anaesthesia Scand.*, vol. 47, pp. 397-406 (2003).

Grandjean et al., "Hydration: issues for the $21^{st}$ century", *Nutrition Reviews*, 61(8):261-271 (2003).

Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).

Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp.-1471-1477 (2003).

Kemming, G.I., et al., "Hyperoxic ventilation at the critical haematocrit," *Resuscitation*, vol. 56, pp. 289-297 (2003).

Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol., 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, ppl 185-190 (Apr. 2003).

Mentes, Janet C., et al., "Reducing Hydration=-Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

Petäjä L., et al., "Dielectric constant of skin and subcutaneous fat to assess fluid changes after cardiac surgery", *Physiological Measurement*, 24: 3383-390, 2003.

Richardson, Andrew D., et al., "Multivariate analyses of visible/near infrared (VIS/NIR) absorbance spectra reveal underlying spectral differences among dried, ground confier needle samples from different growth environments," *New Phytologist*, vol. 161, pp. 291-301 (2003).

Robinson, Martin P., et al., "A novel method of studying total body water content using a resonant cavity: experiments and numerical simulation," *Phys. Med. Biol.*, vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinol. Metab*, vol. 284, pp. E267-E273 (2003).

Windberger, U, et al., "Whole blood viscosity, plasma viscosity and erythrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Ackland, G.L., et al., "Assessment of preoperative fluid depletion using bioimpedance analysis," *British Journal of Anaesthesia*, vol. 92, No. 1, pp. 134-136 (2004).

Arimoto et al., "Non-contact skin moisture measurement based on near-infrared spectroscopy", *Applied Spectroscopy*, 58(12):1439-1445 (2004).

Davidhizr, R., et al., "A review of the literature on how important water is to the world's elderly population," *International Nursing Review*, vol. 51, pp. 159-166 (2004).

Dullenkopf, A., et al., "Non-invasive monitoring of haemoglobin concentration in paediatric surgical patients using near-infrared spectroscopy," *Anaesthesia*, vol. 59, pp. 453-458 (2004).

Finlay, Jarod C., et al., "Hemoglobin oxygen saturations in phantoms and in vivo from measurements of steady-state diffuse reflectance at a single, short source-detector separation," *Medical Physics*, vol. 31, No. 7, pp. 1949-1959 (Jul. 2004).

Hendriks, F.M., et al., "Influence of hydration and experimental length scale on the mechanical response o human skin in vivo, using optical coherence tomography," *Skin Research and Technology*, vol. 10, pp. 231-241 (2004).

Hieda, I., et al., "Basic characteristics of the radio imaging method for biomedical application," *Medical Engineering & Physics*, vol. 26, pp. 431-437 (2004).

Ikizler, T. Alp, et al., "Urea space and total body water measurements by stable isotopes in patients with acute renal failure," *Kidney International*, vol. 65, pp. 725-732 (2004).

Isenring, E., et al., "Evaluation of foot-to-foot bioelectrical impedance analysis for the prediction of total body water in oncology outpatients receiving radiotherapy," *European Journal of Clinical Nutrition*, vol. 58, pp. 46-51 (2004).

Jacobi, Ute, et al., "In vivo determination of skin surface topography using an optical 3D device," *Skin Research and Technology*, vol. 10, pp. 207-214 (2004).

Kao, Bunsho, et al., "Evaluation of Cryogen Spray Cooling Exposure on in Vitro Model Human Skin," *Lasers in Surgery and Medicine*, vol. 34, pp. 146-154 (2004).

Kyle, Urusula G., et al., Bioelectrical impedance anslysis—part II: utilization in clinical practice, *Clinical Nutrition*, vol. 23, pp. 1430-1453 (2004).

Lof, Marie, et al., "Hydration of fat-free mass in healthy women with special reference to the effect of pregnancy," *Am J. Clin. Nutr.*, vol. 80, pp. 960-965 (2004).

Lowrie, Edmund G., "Urea space and body water," *Kidney Intl.*, vol. 66, No. 2, p. 868, Aug. 2004.

Mirrashed, F., et al., "Pilot study of dermal and subcutaneous fat structures by MRI in individuals who differ in gender, BMI, and cellulite grading," *Skin Research and Technology*, vol. 10, pp. 161-168 (2004).

Mirrashed, Fakhereh, et al., "In vivo morphological characterization of skin by MRI micro-imaging methods," *Skin Research and Technology*, vol. 10, pp. 149-160, (2004).

Notingher, Ioan, et al., "Mid-infrared in vivo depth-profiling of topical chemicals on skin," *Skin Research and Technology*, vol. 10, pp. 113-121, (2004).

Nouveau-Richard, S., et al., "In vivo epidermal thick ness measurement: ultrasound vs. confocal imaging," *Skin Research and Technology*, vol. 10, pp. 136-140, (2004).

Nuutinen, J., et al., "Validation of a enw dielectric device to assess changes of tissue water in skin and subcutaneous fat," *Physiol. Meas.*, vol. 25, pp. 447-454, (2004).

St-Onge, Marie-Pierre, et al., "Dual-energy X-ray absorptiometry lean soft tissue hydration: independent contributions of intra-and extracellular water," *Am J. Physiol. Endrocrinol Metab*, vol. 287, pp. E842-E847, Jul. 6, 2004.

Schou, A. J., et al., "Methodological aspects of high-frequency ultrasound of skin in children," *Skin Research and Technology*, vol. 10, pp. 200-206, (2004).

Stone, Darren A., et al., "Total body water measurements using resonant cavity perturbation techniques," *Phys. Med. Biol.*, vol. 49, pp. 1773-1788, (2004).

Takiwaki, Hirotsugu, et al., "Analysis of the absorbance spectra of skin lesions as a helpful tool for detection of major pathophysiological changes," *Skin Research and Technology*, vol. 10, pp. 130-135 (2004).

Van Kemenade, Patricia M., et al., "Do somotic forces play a role in the uptake of water by human skin?", *Skin Research and Technology*, vol. 10, pp. 109-112 (2004).

Wang, Zimian, et al., "Body cell mass: model development and validation at the cellular level of body composition," *Am J. Physiol. Endocrinol. Metab.*, vol. 286, pp. E123-E128 (2004).

Arimoto, Hidenobu, et al., "Depth profile of diffuse reflectance near-infrared spectroscopy for measurement of water content in skin," *Skin Research and Technology*, vol. 11, pp. 27-35 (2005).

Burmeister, J.J., et al., "Spectroscopic considerations for noninvasive blood glucose measurements with near infrared spectroscopy", *LEOS Newsletter*, vol. 12, No. 2, 1998, http://www.ieee.org/organizations/pubs/newsletters/leos/apr98/infrared.htm (last accessed, Nov. 30, 2005).

Haroun, D., et al., "Composition of the fat-free mass in obese and nonobese children: matched case—control analyses," *International Journal of Obesity*, vol. 29, pp. 29-36 (2005).

Ivorra, Antoni, et al., "Bioimpedance dispersion width as a parameter to monitor living tissues," *Physiol. Meas.*, vol. 26, pp. S165-S173 (2005).

Remote ICU Monitoring, *U.S. News & World Report*, pp. 45-61 (Aug. 1, 2005).

Sarkar, Shubho R., et al., "Assessment of Body Composition in Long-Term Hemodialysis Patients: Rationale and Methodology," *Journal of Renal Nutrition*, vol. 15, No. 1, pp. 152-158 (Jan. 2005).

Youcef-Toumi K., et al., "Noninvasive blood glucose analysis using near infrared absorption spectroscopy", MIT Home Automation and Healthcare Consortium, Progress Report No. 2-5, http://darbelofflab.mit.edu/ProgressReports/HomeAutomation/Report2-5/Chapter04.cdf (last accessed, Nov. 30, 2005).

Garcia-Olmo, J., et al., "Advantages and disadvantages of multiple linear regression and partial least squares regression equations for the prediction of fatty acids," pp. 253-258 (undated).

Wang, Zimian, et al., "Cellular-Level Body Composition Model—A New Approach to Studying Fat-free Mass Hydration," *Annals New York Academy of Sciencei*, pp. 306-311 (undated).

J. H. Ali, et al.; "Near Infrared Spectroscopy and Imaging to Prove differences in Water content in normal and Cancer Human Prostate Tissues," *Technology in Cancer Research & Treatment*, vol. 3, No. 5, Oct. 2004; pp. 491-497.

A.E.R Young, et al.; "Behavior of near-infrared light in the adult human head: Implications of clinical near-infrared spectroscopy," British Journal of Anaesthesia, vol. 84, No. 1, pp. 38-42 (2000).

T. Kurita, et al.; "Comparison of isoflurane and propofol-fentanyl anaesthesia in a swine model of asphyxia"; British Journal of Anaesthesia, vol. 91, No. 6, pp. 871-877 (2003).

P. Mauran, et al.; "Renal and hormonal responses to isotonic saline infusion after 3 days' dead-down tilt vs. supine and seated positions"; Acta Pysiol. Scan., vol. 177, pp. 167-176 (2003.

A. Rhodes, et al.; "Book Report—Haemodynamic monitoring in critically ill patients"; Critical Care, vol. 8, p. 203 (2004).

\* cited by examiner

SYSTEM AND METHOD FOR VENOUS PULSATION DETECTION USING NEAR INFRARED WAVELENGTHS

BACKGROUND OF THE INVENTION

1. Field of the Invention

The present invention relates to pulse oximetry. More particularly, embodiments of the present invention relate to processing of signals generated by a pulse oximeter.

2. Description of the Related Art

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Sensors exist that are designed to be applied to a patient's forehead. However, a phenomenon called "venous pulsation" may occur in the forehead or other sites that are not on the patient's extremities and cause incorrect sensor readings. Venous pulsation refers to a pulse generated from the return flow of venous blood to the heart. Because the hemoglobin in venous blood has already delivered oxygen to tissue, and due to prominent harmonics in a venous pressure wave, sensor readings based on venous pulsation may result in artificially low calculations of blood oxygen saturation. In addition, pulse rate calculations based on incorrect sensor readings may be double or triple the patient's actual pulse rate.

While the reliability of traditional pulse oximetry techniques may be adversely impacted by artifacts caused by venous pulsation, traditional techniques may fail to recognize venous pulsation as the source of an error. In some cases, physiological parameters may be calculated in the presence of venous pulsation for hours without any indication that the resulting values are incorrect.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

There is provided a method for detecting venous pulsation, including acquiring a first signal corresponding to absorption at a first near-infrared wavelength, acquiring a second signal corresponding to absorption at a second near-infrared wavelength, deriving an offset metric from the first and second signals, and detecting the presence of venous pulsation based on the offset metric.

There is further provided a device for detecting venous pulsation, including a monitor configured to acquire a first signal corresponding to absorption at a first near-infrared wavelength and a second signal corresponding to absorption at a second near-infrared wavelength, derive an offset metric from the first and second signals, and detect the presence of venous pulsation based on the offset metric.

There is further provided a system for detecting venous pulsation, including a sensor configured to emit light at three or more wavelengths into a patient's tissue and detect absorption of the light, and a monitor configured to acquire a first signal corresponding to absorption at a first near-infrared wavelength and a second signal corresponding to absorption at a second near-infrared wavelength, derive an offset metric from the first and second signals, and detect the presence of venous pulsation based on the offset metric.

There is further provided a method of manufacturing a device for detecting venous pulsation, including providing a monitor configured to acquire a first signal corresponding to absorption at a first near-infrared wavelength and a second signal corresponding to absorption at a second near-infrared wavelength, derive an offset metric from the first and second signals, and detect the presence of venous pulsation based on the offset metric.

BRIEF DESCRIPTION OF THE DRAWINGS

Advantages of the invention may become apparent upon reading the following detailed description and upon reference to the drawings in which.

DETAILED DESCRIPTION OF SPECIFIC EMBODIMENTS

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present invention relate to detecting the presence of venous pulsation, when using a forehead pulse oximetry sensor for example, and correcting the errors associated with venous pulsation in calculating a patient's physiological parameters, such as blood oxygen saturation and pulse rate. Specifically, in accordance with present embodiments, a sensor emits and detects a near-infrared wavelength of light in addition to the red and near-infrared wavelengths commonly used to calculate physiological parameters. This third wavelength of light is used to determine whether venous pulsation is occurring and to correct measurements of the commonly used red and near-infrared wavelengths of light when venous pulsation occurs.

In accordance with an exemplary embodiment of the present invention, arterial blood oxygen saturation, commonly denoted as $SaO_2$, may be estimated as a ratio of oxygenated hemoglobin ($HbO_2$) to deoxygenated hemoglobin (Hb) present in a patient's tissue. Hemoglobin is the component of blood which transports oxygen throughout the body. The ratio of $HbO_2$ to Hb can be determined by shining light at certain wavelengths into a patient's tissue and measuring the absorbance of the light. A first wavelength is typically selected at a point in the electromagnetic spectrum where the absorption of $HbO_2$ differs from the absorption of reduced Hb, and a second wavelength is typically selected at a different point in the spectrum where the absorption of Hb and $HbO_2$ differs from those at the first wavelength. For example, wavelength selections for measuring normal blood oxygenation levels typically include a red light emitted at approximately 660 nm and a near-infrared light emitted at approximately 900 nm, although other red and near-infrared wavelengths may be used. A yellow or orange wavelength may be utilized instead of, or in addition to, the red wavelength.

One common technique for estimating $SaO_2$ is to calculate a characteristic known as the ratio-of-ratios (Ratrat) of the absorption of the red light (RED) to the near-infrared light (IR). While various techniques may be utilized to calculate Ratrat, in one common technique in accordance with an exemplary embodiment of the present invention, a sensor is used to emit red and near-infrared light into a patient's tissue and detect the light that is reflected back. Signals indicative of the detected light are conditioned and processed to generate plethysmographs of the detected light over time. A plethysmographic waveform is generally periodic, with a shape between that of a sawtooth and a sinusoid, having both an AC and a DC component. These AC and DC components may be estimated from maximum (MAX) and minimum (MIN) points in a cycle of the waveform, according to the following equations:

$$AC = MAX - MIN, \quad (1)$$

$$DC = (MAX + MIN)/2. \quad (2)$$

It should be noted that in other embodiments the maximum and minimum measurements are not necessarily employed to determine the AC and DC components. Indeed, the AC and DC components may be obtained by using essentially any pair of points along both the red and near-infrared light waveforms. The AC and DC components of the RED wavelength and IR wavelength signals may then be used to calculate Ratrat according to the following equation:

$$Ratrat = \frac{AC_{RED}/DC_{RED}}{AC_{IR}/DC_{IR}}. \quad (3)$$

Ratrat has been observed to correlate well to $SaO_2$. This observed correlation is used to estimate $SaO_2$ based on the measured value of the ratio-of-ratios. This pulse-based estimate of $SaO_2$ is commonly denoted as $SpO_2$.

Figure 1:
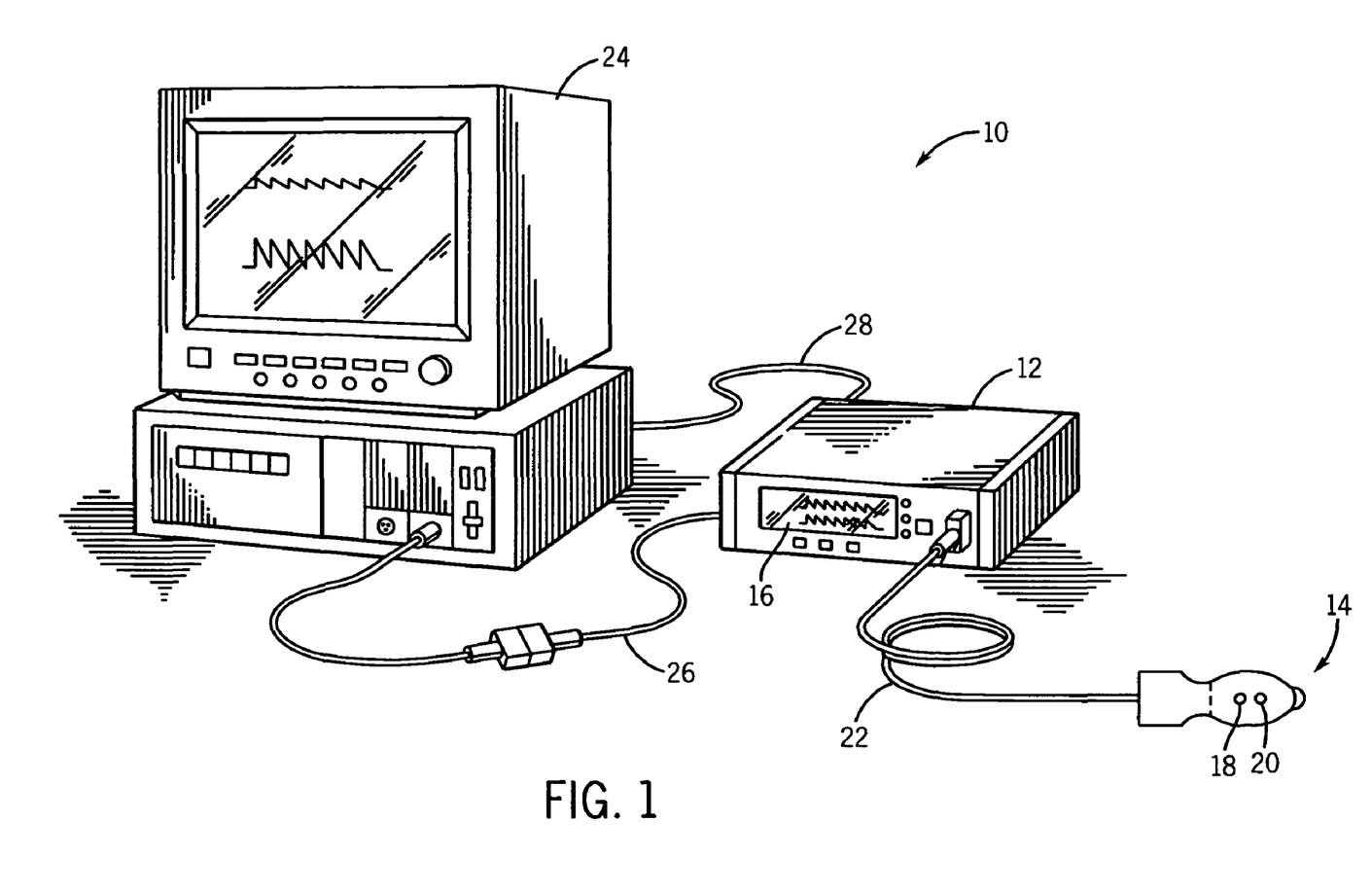
FIG. 1 is a perspective view of a pulse oximetry monitor coupled to a multi-parameter patient monitor and a sensor in accordance with an exemplary embodiment of the present invention.

FIG. 1 is a perspective view of a pulse oximetry system 10 in accordance with an exemplary embodiment of the present invention. The system 10 may include a pulse oximetry monitor 12 and a sensor 14. The monitor 12 may be configured to calculate values for physiological parameters, as described below, and to display physiological parameters and/or other information about the system on a display 16. The sensor 14 may include an emitter 18 for emitting light at certain wavelengths into a patient's tissue and a detector 20 for detecting the light after it is scattered and reflected by the patient's tissue. The sensor 14 may be communicatively coupled to the monitor 12 via a cable 22 or other suitable means, such as, for example, a wireless transmission device (not shown).

The pulse oximetry system 10 may also include a multi-parameter patient monitor 24. The multi-parameter patient monitor 24 may be included in the system 10 to provide a central display for information from the monitor 12 and from other medical monitoring devices or systems (not shown). For example, the multi-parameter patient monitor 24 may display a patient's blood oxygen saturation and pulse rate information from the monitor 12 and blood pressure from a blood pressure monitor (not shown). In addition to the monitor 12, or alternatively, the multi-parameter patient monitor 24 may be configured to calculate values for physiological parameters, as described below. The monitor 12 may be communicatively coupled to the multi-parameter patient monitor 24 via a cable 26 or 28 coupled to a sensor input port or a digital communications port, respectively.

Figure 2:
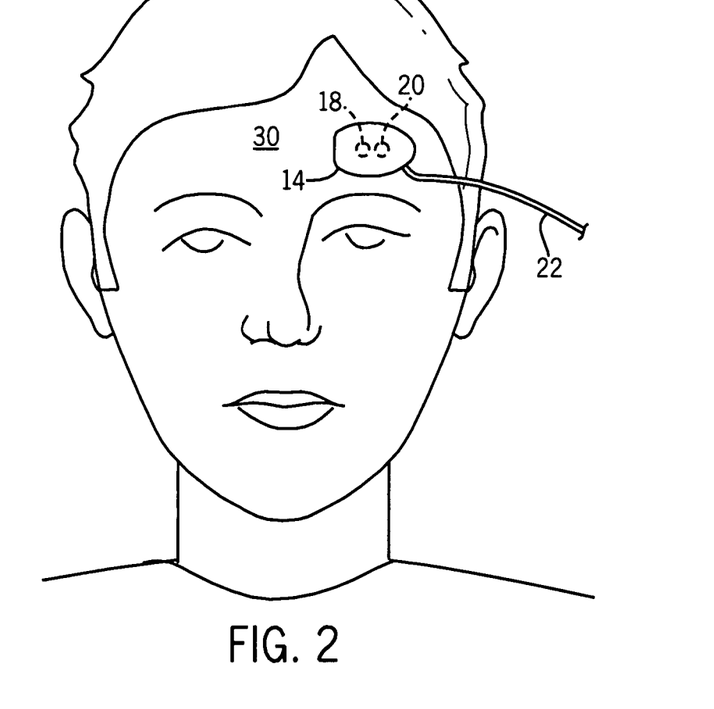
FIG. 2 illustrates a sensor applied to a patient's forehead in accordance with an exemplary embodiment of the present invention.

FIG. 2 illustrates the sensor 14 applied to a patient's forehead 30 in accordance with an exemplary embodiment of the present invention. The sensor 14 may include components to facilitate venous pulsation detection and/or compensation for related measurement errors as set forth below. Venous pulsation is more likely to occur when the sensor 14 is applied to a patient's forehead 30 as illustrated, without any external pressure applied to the sensor site. A headband (not shown) may be placed over the sensor 14 to reduce the effects of venous pulsation on the calculation of a patient's physiological parameters.

Figure 3:
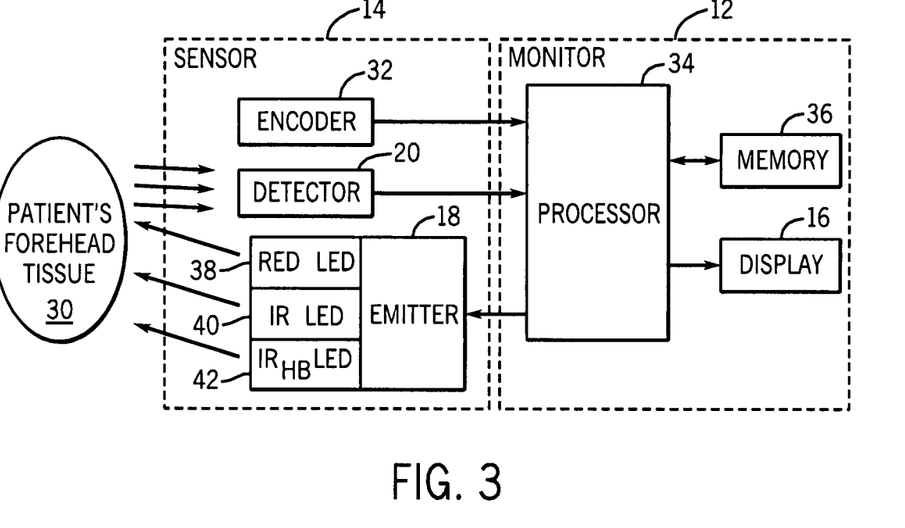
FIG. 3 is a block diagram of a pulse oximetry system coupled to a patient in accordance with an exemplary embodiment of the present invention.

FIG. 3 is a block diagram of the pulse oximetry system 10 in accordance with an exemplary embodiment of the present invention. Components of the monitor 12 and the sensor 14 are illustrated. The sensor 14 includes emitter 18, detector 20, and an encoder 32. Furthermore, emitter 18 is configured to emit at least three wavelengths of light. Monitor 12 includes a processor 34, a memory 36, and display 16.

In accordance with an exemplary embodiment of the present invention, the emitter 18 includes a RED LED 38, an IR LED 40, and an $IR_{Hb}$ LED 42 for emitting light at the wavelengths required to calculate values for physiological parameters, as described below. Alternative light sources may be used in other embodiments of the present invention. For example, a single wide-spectrum light source may be used, and the detector 20 may be configured to detect light only at certain wavelengths. Alternatively, the detector 20 may detect a wide spectrum of wavelengths of light, and the monitor 12 may process only those wavelengths which are of interest. The emitter 18 may shine light at the different wavelengths into the patient's forehead tissue 30.

The detector 20 may be configured to detect the intensity of light at the RED, IR, and $IR_{Hb}$ wavelengths in accordance with an exemplary embodiment of the present invention. Light enters the detector 20 after reflecting off tissue in the patient's forehead 30. The detector 20 may measure the intensity of light at each wavelength of interest and convert that measurement into a digital signal. The light intensity is directly related to the absorbance of light in the tissue 30. That is, when more light at a certain wavelength is absorbed, less light of that wavelength is reflected back and detected by the detector 20. After measuring the light and converting it to a digital signal, the detector 20 may send the signal to the monitor 12.

The encoder 32 may contain information about the wavelengths of light emitted by the emitter 18. This information may allow the monitor 12 to select appropriate calibration coefficients for calculating the patient's physiological parameters. The encoder 32 may, for instance, be a resistor. In addition, the encoder 32 may include information about the sensor 14, such as, for example, that it is a forehead sensor. Any information the encoder 32 contains may be communicated to the monitor 12 for processing along with the information about the detected light from detector 20.

The processor 34 in the monitor 12 may be configured to process incoming signals from and send control signals to the sensor 14. Intermediate hardware (not shown) may be included in the monitor 12 to filter or convert incoming signals and to implement outgoing controls. The memory 36 may contain programming to enable processor 34 to calculate values for physiological parameters, as described below, and to implement the process described below in relation to FIG. 5. In addition, results of such calculations may be stored on the memory 36 and/or displayed on the display 16. The display 16 may also provide a visual notification of the presence of venous pulsation when detected.

Recent trials were run in which wide spectrum light was shone into subjects' forehead tissues and the reflectance/absorbance was detected. It was observed from analysis of these trials that the AC signal contains a generally wavelength-independent offset which does not appear to correlate with light absorption in principal blood or tissue components that are typically intended to be measured. This offset was much higher when the subjects were placed in a position in which venous pulsation was likely to occur than when they were not. The addition of a positive wavelength-independent offset to the AC amplitude causes the Ratrat to converge towards a value near 1.0, regardless of the actual $SaO_2$. For typical pulse-oximetry wavelengths, a Ratrat of 1.0 corresponds to an $SaO_2$ near 80%, while a normal adult breathing room air has an $SaO_2$ near 97%. These wavelength-independent offsets in AC amplitude may cause biases in the $SpO_2$ calculation, which are often seen when venous pulsation is present.

Figure 4:
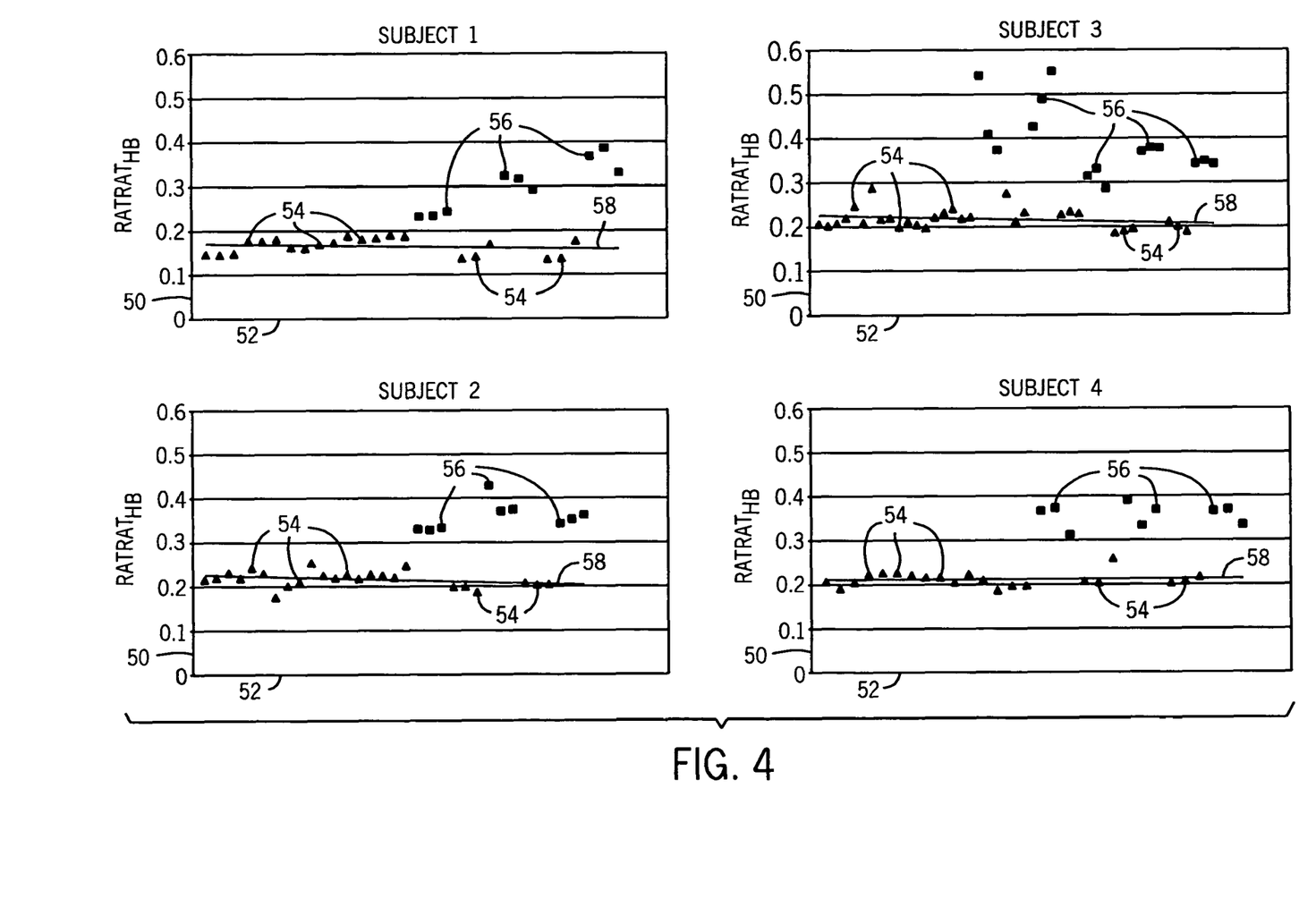
FIG. 4 includes four graphs showing plots of results obtained in detecting venous pulsations in each of four subjects.

The plots shown in FIG. 4 are a graphic illustration of the results of trials testing the detection of venous pulsation in four subjects. In the trials, subjects were monitored using forehead sensors as they were placed into erect positions (i.e., head above heart) and Trendelenburg positions (i.e., heart above head). The Trendelenburg position has been observed to cause venous pulsation in the forehead when no steps are taken to prevent this phenomenon. This data was collected with a sensor having an emitter-detector separation of approximately 2.5 mm. The ratio-of-ratios was calculated for a near-infrared wavelength at which hemoglobin has a low absorption ($IR_{Hb}$) to the near-infrared wavelength used to estimate $SpO_2$ (IR), as illustrated in the following equation:

$$Ratrat_{Hb} = \frac{AC_{IRHb}/DC_{IRHb}}{AC_{IR}/DC_{IR}}. \quad (4)$$

The calculated $Ratrat_{Hb}$ was found to correlate to the presence of venous pulsation.

At wavelengths where hemoglobin has a low absorption, the AC offset is expected to be primarily due to the effects of venous pulsation. Hemoglobin has a sufficiently low absorption at a wavelength in the range of 1,050-1,350 nm. Due to local water and blood pooling, changes in the water component of the AC spectrum were also observed in some subjects. So that these water changes do not confound the detection of venous pulsation, it may be desirable to further narrow the wavelength range to about 1,050-1,160 nm. FIG. 4 illustrates $Ratrat_{Hb}$ calculated where $IR_{Hb}$ is 1,126 nm and IR is 918 nm.

In the graphs illustrated in FIG. 4, the $Ratrat_{Hb}$ of the selected wavelengths are plotted on the y-axis 50 against time on the x-axis 52. Data points 54 represent the calculated $Ratrat_{Hb}$ when a subject was in an erect position, and data points 56 represent the calculated $Ratrat_{Hb}$ when a subject was in the Trendelenburg position. When pressure is not applied to a forehead sensor, as in these trials, it can be assumed that placing a subject in the Trendelenburg position will cause venous pulsation. As can be seen from the graphs in FIG. 4, the $Ratrat_{Hb}$ was substantially higher for each subject when venous pulsation was likely to be present (data points 56) than when it was not (data points 54). In addition, the $Ratrat_{Hb}$ was generally consistent when venous pulsation was not likely to be present (data points 54), as illustrated by trendline 58.

Figure 5:
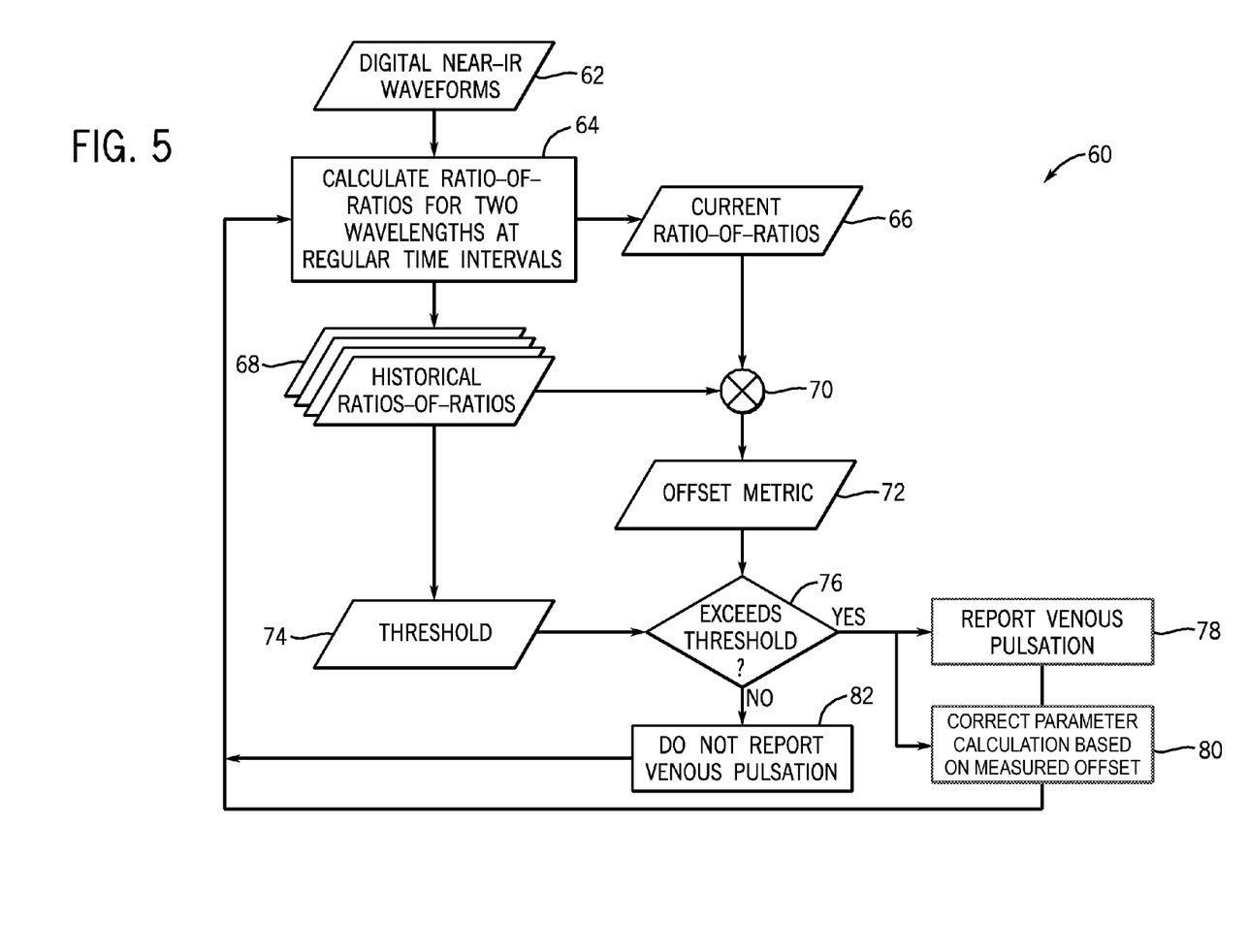
FIG. 5 is a flow chart of a process related to detecting venous pulsations in accordance with an exemplary embodiment of the present invention.

As a result of these studies, an offset metric may be derived to predict the presence of venous pulsation in subjects with more accuracy than that seen with previous methods of detecting venous pulsation. This offset metric may be the $Ratrat_{Hb}$ itself or a change in $Ratrat_{Hb}$ from historical values ($\Delta Ratrat_{Hb}$). FIG. 5 is a flow chart of a process 60 in accordance with an exemplary embodiment of the present invention. In this process 60, the presence of venous pulsation is detected based on the offset metric.

As illustrated in FIG. 5, at least two digital near-IR waveforms 62 are provided. These waveforms 62 correspond to detected light at the IR and $IR_{Hb}$ wavelengths. The $Ratrat_{Hb}$ is calculated (Block 64) for $IR_{Hb}$ to IR, for example, as described above in Eq. 4. A current $Ratrat_{Hb}$ 66 may be compared (Block 70) to historical values 68 of $Ratrat_{Hb}$. The historical values 68 may include actual values calculated from a given patient or average values calculated from other subjects. In an exemplary embodiment of the present invention, the process 60 may use average values as the historical values 68. Once enough data has been collected to provide a reliable baseline for an individual patient, that patient's actual measurement data may be utilized as the historical values 68. In addition, the historical values 68 may be represented as an average, weighted average, mean, median, or mode.

An offset metric 72 may be derived from the current Ratrat$_{Hb}$ 66 and the historical values 68. This offset metric 72 may be the difference between the current Ratrat$_{Hb}$ 66 and the historical values 68, denoted ΔRatrat$_{Hb}$, the current Ratrat$_{Hb}$ 66, or a combination thereof. The offset metric 72 may be compared to a threshold 74 to determine if the threshold 74 is exceeded (Block 76). Threshold 74 may be a pre-determined value or may be based on the historical values 68 of the Ratrat$_{Hb}$. For example, in accordance with an exemplary embodiment of the present invention, threshold 74 may be a fixed value for all patients above which venous pulsation is expected to be present. Alternatively, threshold 74 may be a fixed value based on a patient's physical characteristics, such as, for example, sex, weight, race, and age. In accordance with another embodiment, threshold 74 may be a change from a patient's actual historical values 68. That is, threshold 74 may be a fixed value or percentage above a baseline of a patient's historical values 68.

If the offset metric 72 exceeds the threshold 74, the presence of venous pulsation may be reported (Block 78). Reporting venous pulsation (Block 78) may include any suitable method, such as, for example, displaying an error message, sounding an audible alarm, or ceasing display of physiological parameters. Alternatively, or in addition to reporting the presence of venous pulsation (Block 78), corrections may be made in the calculation of other physiological parameters (Block 80) based on the measured AC offset. For example, the AC offset detected in the IR$_{Hb}$ wavelength may be corrected for the RED and IR wavelengths by subtracting it from the AC measurements at those wavelengths before physiological parameters are calculated.

If the offset metric 72 does not exceed the threshold 74, the presence of venous pulsation may not be reported (Block 82). Regardless of the outcome of the comparison (Block 76) of the offset metric 72 to the threshold 74, the process 60 continues by returning to the calculation of Ratrat$_{Hb}$ (Block 64) for new detected measurements of IR and IR$_{Hb}$.

While the invention may be susceptible to various modifications and alternative forms, specific embodiments have been shown by way of example in the drawings and have been described in detail herein. However, it should be understood that the invention is not intended to be limited to the particular forms disclosed. Indeed, the but these techniques may not only be applied to measurements of blood oxygen saturation, but these techniques may also be utilized for the measurement and/or analysis of other blood constituents. For example, using the same, different, or additional wavelengths, the present techniques may be utilized in conjunction with the measurement and/or analysis of carboxyhemoglobin, methemoglobin, total hemoglobin, intravascular dyes, and/or water content. The invention is to cover all modifications, equivalents, and alternatives falling within the spirit and scope of the invention as defined by the following appended claims.

What is claimed is:

1. A method for detecting venous pulsation, comprising:
    acquiring a first signal corresponding to absorption at a first near-infrared wavelength from a sensor;
    acquiring a second signal corresponding to absorption at a second near-infrared wavelength from the sensor;
    deriving an offset metric from the first and second signals with a processor, wherein the offset metric comprises a difference between current and historical values of a ratio-of-ratios of the absorption at the first near-infrared wavelength to the absorption at the second near-infrared wavelength; and
    detecting the presence of venous pulsation based on comparing the offset metric with a threshold value and determining whether the offset metric exceeds the threshold value using the processor.

2. The method of claim 1, comprising providing, with a monitor, a notification of the presence of venous pulsation when detected.

3. The method of claim 1, comprising acquiring a third signal corresponding to absorption at a third wavelength from the sensor and calculating a physiological parameter with the processor based on the second and third signals.

4. The method of claim 3, comprising correcting, with the processor, the calculation of the physiological parameter by subtracting an AC offset of the third signal from an AC measurement of the second signal utilized in the calculation of the physiological parameter.

5. The method of claim 3, wherein the second near-infrared wavelength comprises a wavelength of about 900 nm and wherein the third wavelength comprises a wavelength of about 660 nm.

6. The method of claim 1, wherein the first near-infrared wavelength comprises a wavelength in a range of 1,050 to 1,350 nm where hemoglobin has a lower absorption than at the second near-infrared wavelength, which comprises a wavelength of approximately 900 nm.

7. The method of claim 6, wherein the wavelength of approximately 900 nm is 918 nm.

8. The method of claim 1, wherein the first near-infrared wavelength comprises a wavelength from 1,050 to 1,350 nm.

9. The method of claim 1, wherein the first near-infrared wavelength comprises a wavelength from 1,050 to 1,160 nm.

10. The method of claim 1, wherein the threshold value comprises at least one of a fixed value or a value based on a plurality of historic ratios-of-ratios.

11. A device for detecting venous pulsation, comprising: a monitor configured to:
    acquire a first signal corresponding to absorption at a first near-infrared wavelength and a second signal corresponding to absorption at a second near-infrared wavelength;
    derive an offset metric from the first and second signals, wherein the offset metric comprises a difference between current and historical values of a ratio-of-ratios of the absorption at the first near-infrared wavelength to the absorption at the second near-infrared wavelength; and
    detect the presence of venous pulsation based on comparing the offset metric with a threshold value and determining whether the offset metric exceeds the threshold value.

12. The device of claim 11, wherein the monitor is configured to provide a notification of the presence of venous pulsation when detected.

13. The device of claim 11, wherein the monitor is configured to acquire a third signal corresponding to absorption at a third wavelength and to calculate a physiological parameter based on the second and third signals.

14. The device of claim 13, wherein the monitor is configured to correct the calculation of the physiological parameter by subtracting an AC offset of the third signal from an AC measurement of the second signal utilized in the calculation of the physiological parameter.

15. A system for detecting venous pulsation, comprising: a sensor configured to:

emit light at three or more wavelengths into a patient's tissue; and detect absorption of the light; and a monitor configured to:

acquire a first signal from the sensor corresponding to absorption at a first near-infrared wavelength and a second signal from the sensor corresponding to absorption at a second near-infrared wavelength;

derive an offset metric from the first and second signals, wherein the offset metric comprises a difference between current and historical values of a ratio-of-ratios of the absorption at the first near-infrared wavelength to the absorption at the second near-infrared wavelength; and detect the presence of venous pulsation based on comparing the offset metric with a threshold value and determining whether the offset metric exceeds the threshold value.

16. The system of claim 15, wherein the first near-infrared wavelength comprises a wavelength in a range of 1,050 to 1,350 nm where hemoglobin has a lower absorption than at the second near-infrared wavelength, which comprises a wavelength of approximately 900 nm.

17. The system of claim 16, wherein the wavelength of approximately 900 nm is 918 nm.

18. The device of claim 15, wherein the three or more wavelengths comprise about 660 nm, about 900 nm, and about 1,126 nm.

19. The device of claim 15, wherein the monitor is configured to provide a notification of the presence of venous pulsation when detected.

20. The device of claim 15, wherein the monitor is configured to acquire a third signal corresponding to absorption at a red wavelength from the sensor and to calculate a physiological parameter based on the second and third signals.

21. The device of claim 20, wherein the monitor is configured to correct the calculation of the physiological parameter by subtracting an AC offset of the third signal from an AC measurement of the second signal utilized in the calculation of the physiological parameter.

* * * * *